United States Patent [19]

Bell et al.

[11] Patent Number: 5,591,742

[45] Date of Patent: Jan. 7, 1997

[54] PYRIDOPYRIMIDINONE ANTIANGINAL AGENTS

[75] Inventors: Andrew S. Bell; Nicholas K. Terrett, both of Sandwich, United Kingdom

[73] Assignee: Pfizer Inc., New York, N.Y.

[21] Appl. No.: 379,531

[22] PCT Filed: Aug. 4, 1993

[86] PCT No.: PCT/EP93/02097

§ 371 Date: Jan. 31, 1995

§ 102(e) Date: Jan. 31, 1995

[87] PCT Pub. No.: WO94/05661

PCT Pub. Date: Mar. 17, 1994

[30] Foreign Application Priority Data

Aug. 28, 1992 [GB] United Kingdom ............... 9218322

[51] Int. Cl.⁶ ............... A61K 31/535; A61K 31/435; C07D 413/14; C07D 487/02
[52] U.S. Cl. ............... 514/234.5; 514/258; 544/116; 544/119; 544/279
[58] Field of Search ............... 544/279, 116, 544/119; 514/234.5, 258

[56] References Cited

U.S. PATENT DOCUMENTS

| | | | |
|---|---|---|---|
| 4,039,544 | 8/1977 | Broughton et al. | 514/243 |
| 5,047,404 | 9/1991 | Coates et al. | 514/243 |
| 5,075,310 | 12/1991 | Coates et al. | 514/258 |
| 5,426,107 | 6/1995 | Bell et al. | 514/234.2 |

FOREIGN PATENT DOCUMENTS

| | | |
|---|---|---|
| 0347146 | 6/1989 | European Pat. Off. . |
| 0352960 | 7/1989 | European Pat. Off. . |
| 347146 | 12/1989 | European Pat. Off. . |
| 352960 | 1/1990 | European Pat. Off. . |
| 0463756 | 6/1991 | European Pat. Off. . |
| 463756 | 1/1992 | European Pat. Off. . |

*Primary Examiner*—Matthew V. Grumbling
*Attorney, Agent, or Firm*—Peter C. Richardson; Gregg C. Benson; Robert T. Ronau

[57] ABSTRACT

Compounds of the formula

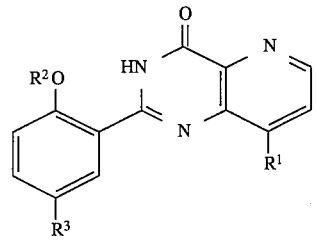

and pharmaceutically acceptable salts thereof, wherein $R^1$ is H, $C_1$–$C_4$ alkyl CN or $CONR^4R^5$; $R^2$ is $C_2$–$C_4$ alkyl; $R^3$ is $SO_2NR^6R^7$, $NO_2$, $NH_2$, $NHCOR^8$ $NHSO_2R^8$ or $N(SO_2R^8)_2$; $R^4$ and $R^5$ are each independently selected from H and $C_1$–$C_4$ alkyl; $R^6$ and $R^7$ are each independently selected from H and $C_1$–$C_4$ alkyl optionally substituted with $CO_2R^9$, OH, pyridyl 5-isoxazolin-3-onyl, morpholino or 1-imidazolidin-2-onyl; or together with the nitrogen atom to which they are attached form a pyrrolidino, piperidino, morpholino, 1-pyrazolyl or 4-($NR^{10}$)-1-piperazinyl group wherein any of said groups may optionally be substituted with one or two substituents selected from $C_1$–$C_4$ alkyl, $CO_2R^9$, $NH_2$ and OH; $R^8$ is $C_1$–$C_4$ alkyl or pyridyl; $R^9$ is H or $C_1$–$C_4$ alkyl; and $R^{10}$ is H, $C_1$–$C_4$ alkyl or (hydroxy) $C_2$–$C_3$ alkyl; are selected cGMP PDE inhibitors useful in the treatment of, inter alia, cardiovascular disorders such as angina, hypertension, heart failure and atherosclerosis.

9 Claims, No Drawings

PYRIDOPYRIMIDINONE ANTIANGINAL AGENTS

This is the national stage under 35 U.S.C. §371(c) of Internal Application No. PCT/EP93/02097, having an international filing data of Aug. 4, 1993, which was oridingally filed Aug. 28, 1992 as Great Britain Patent Application No. 9218322.7.

This invention relates to a series of pyrido[3,2-d]pyrimidin-4-ones, which are potent and selective inhibitors of cyclic guanosine 3',5'-monophosphate phosphodiesterase (cGMP PDE), having utility in a variety of therapeutic areas including the treatment of cardiovascular disorders such as angina, hypertension, heart failure and atherosclerosis.

The compounds of the invention exhibit selectivity for inhibition of cGMP PDEs rather than cyclic adenosine 3',5'-monophosphate phosphodiesterases (cAMP PDEs) and, as a consequence of this selective PDE inhibition, cGMP levels are elevated, which in turn can give rise to beneficial anti-platelet, anti-neutrophil, anti-vasospastic and vasodilatory activity, as well as potentiation of the effects of endothelium-derived relaxing factor (EDRF) and nitrovasodilators. Thus the compounds have utility in the treatment of a number of disorders, including stable, unstable and variant (Prinzmental) angina, hypertension, pulmonary hypertension, congestive heart failure, atherosclerosis, conditions of reduced blood vessel patency e.g. post-percutaneous transluminal coronary angioplasty (post-PTCA), peripheral vascular disease, stroke, bronchitis, allergic asthma, chronic asthma, allergic rhinitis, glaucoma, and diseases characterised by disorders of gut motility, e.g. irritable bowel syndrome (IBS).

European patent application EP-A-0347146 discloses certain pyrido[3,2-d]pyrimidin-4-ones which, unlike the compounds of the present invention, contain a monosubstituted phenyl moiety at the 2-position of the said heterobicyclic system. These compounds are reported to be selective cGMP PDE inhibitors with bronchodilator and vasodilator activity of value in combatting asthma, bronchitis, angina, hypertension and congestive heart failure. The compounds of the present invention contain a 2,5-disubstituted phenyl moiety at the 2-position of the pyrido[3,2-d]pyrimidin-4-one bicyclic system and are significantly more potent cGMP PDE inhibitors than the previously mentioned prior art compounds.

The compounds of the present invention have the formula (I):

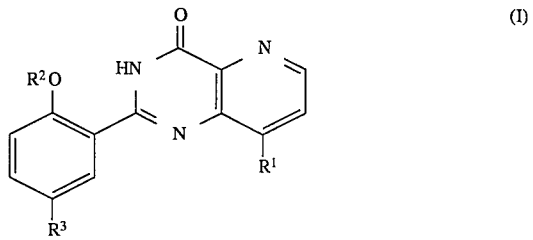

and pharmaceutically acceptable salts thereof, wherein $R^1$ is H, $C_1$–$C_4$ alkyl, CN or $CONR^4R^5$;

$R^2$ is $C_2$–$C_4$ alkyl;

$R^3$ is $SO_2NR^6R^7$, $NO_2$, $NH_2$, $NHCOR^8$, $NHSO_2R^8$ or $N(SO_2R^8)_2$;

$R^4$ and $R^5$ are each independently selected from H and $C_1$–$C_4$ alkyl;

$R^6$ and $R^7$ are each independently selected from H and $C_1$–$C_4$ alkyl optionally substituted with $CO_2R^9$, OH pyridyl 5-isoxazolin-3-onyl, morpholino or 1-imidazolidin-2-onyl; or together with the nitrogen atom to which they are attached form a pyrrolidino, piperidino, morpholino, 1-pyrazolyl or 4-($NR^{10}$)-1-piperazinyl group wherein any of said groups may optionally be substituted with one or two substituents selected from $C_1$–$C_4$ alkyl, $CO_2R^9$, $NH_2$ and OH;

$R^8$ is $C_1$–$C_4$ alkyl or pyridyl;

$R^9$ is H or $C_1$–$C_4$ alkyl;

and $R^{10}$ is H, $C_1$–$C_4$ alkyl or (hydroxy) $C_2$–$C_3$ alkyl.

In the above definition, unless otherwise indicated, alkyl groups having three or more carbon atoms may be straight chain or branched chain.

The compounds of formula (I) may contain one or more asymmetric centres and thus they can exist as stereoisomers, i.e. as enantiomers or as diastereoisomers. The invention includes both mixtures thereof and the separated individual stereoisomers.

The compounds of formula (I) may also exist in tautomeric forms and the invention includes both mixtures thereof and the separated individual tautomers.

Also included in the invention are radiolabelled derivatives of compounds of formula (I) which are suitable for biological studies.

The pharmaceutically acceptable salts of the compounds of formula (I) which contain a basic centre are, for example, non-toxic acid addition salts formed with inorganic acids such as hydrochloric, hydrobromic, sulphuric and phosphoric acid, with organo-carboxylic acids, or with organo-sulphonic acids. Compounds of formula (I) can also provide pharmaceutically acceptable metal salts, in particular non-toxic alkali metal salts, with bases. Examples include the sodium and potassium salts. For a review on suitable pharmaceutical salts, see J. Pharm, Sci., 1977, 66, 1.

A preferred group of compounds of formula (I) is that wherein $R^1$ is H, n-propyl, CN or $CONH_2$; $R^2$ is ethyl; $R^3$ is $SO_2NR^6R^7$, $NO_2$, $NH_2$, $NHCOCH(CH_3)_2$, $NHSO_2CH(CH_3)_2$, $NHSO_2$(3-pyridyl) or $N[SO_2$(3-pyridyl)$]_2$; $R^6$ is H, methyl or 2-hydroxyethyl; $R^7$ is methyl optionally substituted with 2-pyridyl or 5-isoxazolin-3-onyl, or ethyl 2-substituted with OH, $CO_2CH_2CH_3$, morpholino or 1-imidazolidin-2-onyl, or $R^6$ and $R^7$ together with the nitrogen atom to which they are attached form a (4-$CO_2R^9$)piperidino, 5-amino-3-hydroxy-1-pyrazolyl or 4-($NR^{10}$)-1-piperazinyl group; $R^9$ is H or ethyl; and $R^{10}$ is H, methyl or 2-hydroxyethyl.

A particularly preferred group of compounds of formula (I) is that wherein $R^1$ is n-propyl or CN; $R^9$ is ethyl; $R^3$ is $SO_2NR^6R^7$, $NHSO_2CH(CH_3)_2$, $NHSO_2$(3-pyridyl) or $N[SO_2$(3-pyridyl)$]_2$; $R^6$ is H or methyl; $R^7$ is methyl, or ethyl 2-substituted with $CO_2CH_2CH_3$, morpholino or 1-imidazolidin-2-onyl, or $R^6$ and $R^7$ together with the nitrogen atom to which they are attached form a (4-$CO_2R^9$) piperidino or 4-($NR^{10}$)-1-piperazinyl group; $R^9$ is H or ethyl; and $R^{10}$ is H, methyl or 2-hydroxyethyl.

Especially preferred individual compounds of the invention include:

2-[2-ethoxy-5-(4-ethoxycarbonylpiperidino-sulphonyl)phenyl]-8-n-propylpyrido[3,2-d]pyrimidin-4(3H)-one;

2-[5-(4-carboxypiperidinosulphonyl)-2-ethoxyphenyl]-8-n-propylpyrido[3,2-d]pyrimidin-4(3H)-one;

2-{2-ethoxy-5-[4-(2-hydroxyethyl)-1-piperazinyl-sulphonyl]phenyl}-8-n-propylpyrido[3,2-d]pyrimidin-4(3H)-one;

and 2-{2-ethoxy-5-[(bis-3-pyridylsulphonyl)amino]-phenyl}-8-n-propylpyrido[3,2-d]pyrimidin-4(3H)-one.

In another aspect, the present invention provides processes for the preparation of compounds of formula (I) and pharmaceutically acceptable salts thereof, as hereinafter described. Depending on the nature of $R^3$, the compounds of formula (I) may be prepared by a variety of methods from a compound of formula (II):

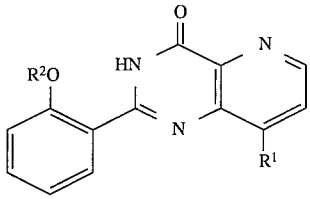

wherein $R^1$ and $R^2$ are as previously defined for formula (I).

(A) A compound of formula (I) wherein $R^3$ is $SO_2NR^6R^7$, wherein $R^6$ and $R^7$ are as previously defined, may be obtained from a compound of formula (II) via the intermediacy of a sulphonyl halide of formula (III):

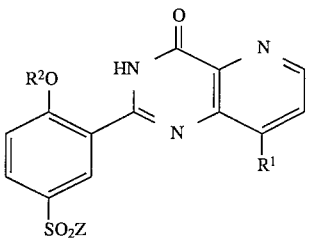

wherein Z is halo, preferably chloro, and $R^1$ and $R^2$ are as previously defined for formula (II), by reaction with an amine of formula (IV):

$HNR^6R^7$ (IV)

wherein $R^6$ and $R^7$ are as previously defined for formula (I). The reaction is generally carried out at ambient temperature, preferably in the presence of a solvent, e.g. a $C_1$–$C_3$ alkanol, using about a 3-fold excess of (IV) to scavenge the acid by-product (HZ) and, in the case of piperazine ($R^{10}$ is H), also to minimise bis-sulphonamide formation.

Certain of these compounds of formula (I), wherein $R^{10}$ is as previously defined but not hydrogen, may be prepared directly from the corresponding 4-N-unsubstituted piperazine analogue, that is the precursor wherein $R^{10}$ is hydrogen, using appropriate standard alkylation procedures.

A compound of formula (III) is obtainable from (II) by the application of known methods for the introduction of a $SO_2Z$ group into a benzene ring; for example, when Z is chloro, by the action of excess chlorosulphonic acid.at from about 0° C. to ambient temperature.

When the $SO_2NR^6R^7$ substituent of the required compound of formula (I) contains a $CO_2R^9$ substituent wherein $R^9$ is H, the said compound is most conveniently obtained from the corresponding ester precursor, i.e. wherein $R^9$ is $C_1$–$C_4$ alkyl. This may be generally achieved by acid-catalysed or base-catalysed hydrolysis or, more specifically, by protonolysis, e.g. when $R^9$ is t-butyl, by using hydrogen chloride or trifluoroacetic acid. A typical base-catalysed hydrolysis involves the use of an alkali metal hydroxide, e.g. sodium hydroxide or potassium hydroxide, in an aqueous $C_1$–$C_3$ alkanol (preferably ethanol) solvent medium, at from ambient temperature to the reflux temperature of the reaction mixture.

(B) A compound of formula (I) wherein $R^3$ is $NO_2$ may be obtained from a compound of formula (II) under typical aromatic nitration condition, e.g. using a concentrated nitric acid/concentrated sulphuric acid combination at from about 0° C. to ambient temperature.

(C) A compound of formula (I) wherein $R^3$ is $NH_2$ may be obtained from the corresponding nitroarene precursor described above in (B) by catalytic hydrogenation or reduction procedures. For example, hydrogenation may be achieved using a palladium on charcoal or Raney nickel catalyst, in a suitable solvent e.g. ethanol, whilst reduction may be carried out using about a 5-fold excess of stannous chloride, in a suitable solvent such as a $C_1$–$C_3$ alkanol, e.g. ethanol, at the reflux temperature of the reaction mixture.

(D) A compound of formula (I) wherein $R^3$ is $NHCOR^8$, wherein $R^8$ is as previously defined for formula (I), may be obtained from the corresponding aminoarene precursor described above in (C) by acylation with either an acyl halide of formula $R^8COZ$, wherein Z is as previously defined, or with an acid anhydride of formula $(R^8CO)_2O$. For example, in the former case, up to about a 50% excess of the acyl halide may be employed in a suitable solvent, e.g. dichloromethane, in the presence of a suitable acid acceptor, e.g. triethylamine or pyridine, at from about 0° C. to ambient temperature. Alternatively, the reaction may be conducted using pyridine as both solvent and acid acceptor. In the latter case, reaction of the aminoarene with up to about a 50% excess of the required acid anhydride may be effected in a suitable solvent, e.g. pyridine, at from about 0° C. to about 100° C.

(E) A compound of formula (I) wherein $R^3$ is $NHSO_2R^8$ or $N(SO_2R^8)_2$, wherein $R^8$ is as previously defined for formula (I), may be obtained from the corresponding aminoarene precursor described above in (C) by sulphonylation with either a sulphonyl halide of formula $R^8SO_2Z$, wherein Z is as previously defined, or with a sulphonic anhydride of formula $(R^8SO_2)_2O$, by direct analogy with the acylation processes described above in (D).

A compound of formula (II) may be prepared from a compound of formula (V):

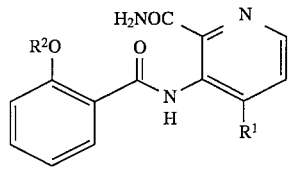

wherein $R^1$ and $R^2$ are as previously defined for formula (II), by the application of known cyclisation methods for pyrimidinone ring formation. Thus, for example, the cyclisation may be effected by the treatment of (V) with a base such as sodium hydroxide or potassium carbonate, optionally in the presence of hydrogen peroxide, in an ethanol-water medium at the reflux temperature of the reaction mixture.

In alternative cyclisation procedures, compounds of formula (II) may be obtained by treatment of (V) either with polyphosphoric acid at about 140° C. or with anhydrous zinc chloride at about 210° C.

More conveniently, a compound of formula (II) wherein $R^1$ is $CONR^4$ and $R^4$ and $R^5$ are as previously defined for formula (I) may be obtained from the nitrile precursor, i.e. the corresponding compound of formula (II) wherein $R^1$ is CN. This may be achieved by firstly hydrolysing the nitrile to the carboxylic acid, e.g. using sodium hydroxide or potassium hydroxide in an aqueous $C_1$–$C_3$ alkanol (preferably ethanol) solvent medium at about the reflux temperature of the reaction mixture. Next, the carboxylic acid may be converted to the required amide either via an intermediate acyl halide or alternatively-activated form of the acid, such as those.used in amino acid coupling procedures, or via e.g.

an intermediate methyl ester or ethyl ester. For example, the acyl chloride may be generated using oxalyl chloride and a catalytic quantity of dimethyl-formamide in dichloromethane, and then converted directly to the amide with an amine of formula $HNR^4R^5$ (VI) under standard conditions, or the acid may be activated using a carbodiimide/1-hydroxybenzotriazole combination in the presence of (VI) in a suitable solvent such as dichloromethane. Alternatively, the methyl ester or ethyl ester may be synthesised by replacing (VI) with methanol or ethanol respectively, and then converted to the required amide by treatment with excess (VI) in a bomb at from about 50° C. to about 100° C.

When $R^1$ is $CONH_2$, such a compound of formula (II) can be obtained directly from the said nitrile precursor, e.g. by treatment with 30% aqueous hydrogen peroxide solution and an alkali metal hydroxide (preferably sodium hydroxide) in an aqueous $C_1$–$C_3$ alkanol (preferably ethanol) solvent medium at about the reflux temperature of the reaction mixture.

A compound of formula (V) may be prepared from a compound of formula (VII):

wherein $R^1$ is as previously defined for formula (V), by reaction with a compound of formula (VIII):

wherein $R^2$ and Z are as previously defined for formula (III).

The reaction is generally carried out using from about 1 to about 2 equivalents of (VIII) in the presence of an excess of a tertiary amine such as triethylamine or pyridine to act as scavenger for the acid by-product (HZ), optionally in the presence of a catalyst such as 4-dimethylaminopyridine, in an inert solvent such as dichloromethane, at from about 0° C. to ambient temperature for 2–24 hours. For convenience, pyridine may also be used as solvent.

Compounds of formula (I) may be obtained more directly from a compound of formula (IX):

wherein $R^2$, $R^3$ and Z are as previously defined, when such acyl halides are readily accessible, by reaction with (VII) and subsequent ring-closure of the product as described above. Clearly this alternative synthetic route will only be appropriate when $R^3$ is compatible with the reaction conditions obtaining in both steps.

The 3-aminopyridine-2-carboxamides of formula (VII), the acyl halides of formulae (VIII) and (IX), and the intermediates employed for introduction of the various $R^3$ substituents into compounds of formula (II) to afford compounds of formula (I), when neither commercially available nor subsequently described, can be obtained either by analogy with the process described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections such that all the compounds defined by formula (I) are obtainable.

The pharmaceutically acceptable acid addition salts of the compounds of formula (I) which contain a basic centre may also be prepared in a conventional manner. For example a solution of the free base is treated with the appropriate acid, either neat or in a suitable solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The biological activities of the compounds of the present invention were determined by the following test methods.

Phosphodiesterase activity

Compound affinities for cGMP and cAMP PDEs are assessed by determination of their $IC_{50}$ values (the concentration of inhibitor required for 50% inhibition of enzyme activity). The PDE enzymes are isolated from rabbit platelets and rat kidney, essentially by the method of W. J. Thompson et al. (Biochem., 1971, 10, 311). The calcium/calmodulin (Ca/CAM)—independent cGMP PDE and the cGMP-inhibited cAMP PDE enzymes are obtained from rabbit platelets whilst, of the four major PDE enzymes of the rat kidney, the Ca/CAM-dependent cGMP PDE (fraction I) is isolated. Assays are performed using a modification of the "batch" method of W. J. Thompson and M. M. Appleman (Biochem., 1979, 18, 5228). Results from these tests show that the compounds of the present invention are potent and selective inhibitors of Ca/CAM-independent cGMP PDE.

Platelet anti-aggregatory activity

This is assessed by the determination of a compound's ability to inhibit platelet aggregation in vitro induced by platelet activating factor (PAF), and to potentiate the platelet antiaggregatory action in vitro of activators of guanylate cyclase such as nitroprusside and EDRF. Washed platelets are prepared essentially by the method of J. F. Mustard et al. (Methods in Enzymol., 1989, 169, 3) and aggregation is determined using standard turbidimetric techniques as described by G.V.R. Born, (J. Physiol. (Lond), 1962, 162, 67P).

Antihypertensive activity

This is assessed following intravenous or oral administration of a compound to spontaneously hypertensive rats. Blood pressure is recorded via a cannula implanted in the carotid artery of either conscious or anaesthetised animals.

For administration to man in the curative or prophylactic treatment of the disorders identified on page 1, oral dosages of the compounds will generally be in the range of from 4–800 mg daily for an average adult patient (70 kg). Thus for a typical adult patient, individual tablets or capsules contain from 2–400 mg of active compound, in a suitable pharmaceutically acceptable vehicle or carrier, for administration in single or multiple doses, once or several times per day. Dosages for intravenous, buccal or sublingual administration will typically be within the range of from 1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, or in the form of elixirs or suspensions containing flavouring or colouring agents. The compounds may also be injected parenterally, for example intravenously, intramuscularly, subcutaneously or intracoronarily. For parenteral administration, they are best used in the form of a sterile aqueous solution which may contain other substances, for example salts, or monosaccharides such as mannitol or glucose, to make the solution isotonic with blood.

Thus the invention provides a pharmaceutical composition comprising a compound of formula (I), or a pharmaceutically acceptable salt thereof, together with a pharmaceutically acceptable diluent or carrier.

The invention also provides a compound of formula (I), or a pharmaceutically acceptable salt thereof, or a pharmaceutical composition containing either entity, for use in medicine.

The invention further provides the use of a compound of formula (I), or a pharmaceutically acceptable salt thereof, or a pharmaceutical composition containing either entity, for the manufacture of a medicament for the treatment of stable, unstable and variant (Prinzmetal) angina, hypertension, pulmonary hypertension, congestive heart failure, atherosclerosis, stroke, peripheral vascular disease, conditions of reduced blood vessel patency e.g. post-PTCA, chronic asthma, bronchitis, allergic asthma, allergic rhinitis, glaucoma, or diseases characterised by disorders of gut motility, e.g. IBS.

In a further aspect, the invention provides a method of treating or preventing stable, unstable and variant (Prinzmetal) angina, hypertension, pulmonary hypertension, congestive heart failure, atherosclerosis, stroke, peripheral vascular disease, conditions of reduced blood vessel patency e.g. post-PTCA, chronic asthma, bronchitis, allergic asthma, allergic rhinitis, glaucoma, or diseases characterised by disorders of gut motility, e.g. IBS, in a mammal (including a human being), which comprises administering to said mammal a therapeutically effective amount of a compound of formula (I), or a pharmaceutically acceptable salt thereof, or a pharmaceutical composition containing either entity.

The invention also includes any novel intermediates of formulae (II) and (III) disclosed herein.

The syntheses of the compounds of the invention and of the intermediates for use therein are illustrated by the following Examples and Preparations. The purity of the compounds was routinely monitored by thin layer chromatography (TLC) using Merck Kieselgel 60 $F_{254}$ plates. $^1$H-Nuclear magnetic resonance (NMR) spectra were recorded using either a Nicolet QE-300 or a Bruker AC-300 spectrometer and were in all cases consistent with the proposed structures.

Ambient temperature means 20° C. to 25° C.

EXAMPLE 1

2-[2-Ethoxy-5-(2-morpholinoethylsulphamoyl)phenyl]-8-n-propylprido [3,2,d]pyrimidin-4 (3H) -one 2- ( 2-Ethoxyphenyl ) -8-n-propylpyrido [3,2-d]pyrimidin-4 (3H) -one (Preparation 8; 1.09 g, 0. 00353 mol) was added portion-wise to stirred chlorosulphonic acid (4 ml) under a nitrogen atmosphere at 0° C. The mixture was stirred at ambient temperature for 18 hours and then added cautiously to ice/water (100 g). The resulting white precipitate was collected by filtration, washed with 2-propanol and then with diethyl ether, and used without further purification.

The crude sulphonyl chloride (0.16 g, 0.0004 mol) was added to a stirred solution of 4-(2-aminoethyl)-morpholine (0.156 g, .0.0012 mol) in ethanol (40 ml), and the resulting solution stirred at ambient temperature for 18 hours. The solvent was evaporated under vacuum, the residue suspended in saturated aqueous sodium carbonate solution (20 ml) and this mixture extracted with dichloromethane (3×20 ml). The organic extracts were combined, dried ($Na_2SO_4$) and evaporated under vacuum, and the resulting residue chromatographed on silica gel (4 g) using a methanol in dichloromethane elution gradient (0–5% methanol). Trituration of the product with diethyl ether gave the title compound as an off-white solid (0.05 g, 25%), m.p. 165°–166° C. Found: C,57.34; H,6.15; N,13.57. $C_{24}H_{31}N_5O_5S$ requires C,57.46; H,6.23; N,13.96%.

The following seven compounds were obtained from the same sulphonyl chloride and the appropriate amine by procedures similar to that described in Example 1.

EXAMPLE 2

2-[2-Ethoxy-5(4-methyl-l-piperazinylsulphonyl)phenyl]-8-n-propylrido [3,2-d]pyrimidin-4(3H)-one Obtained using 1-methylpiperazine in 70% yield, m.p. 211°–212° C. Found: C,58.95; H,6.15; N,14.85. $C_{23}H_{29}N_5O_4S$ requires C,58.58; H,6.20; N,14.85%.

EXAMPLE 3

2- [2-Ethoxy-5-(1-piperazinylsulphonyl]phenyl]-8-n-propylprido [3,2-d]pyrimidin-4(3H) -one Obtained using piperazine in 43% yield, m.p. 178°–180° C. Found: C,57.66; H,5.96; N,15.40. $C_{22}H_{27}N_5O_4S$ requires C,57.75; H,5.95; N,15.31%

EXAMPLE 4

2-[2-Ethoxy-5-(4-ethoxycarbonylpiperidinosulphonyl)-phenyl]-8-n-propylprido [3,2-d]pyrimidin-4(3H) -one Obtained using ethyl isonipecotate in 86% yield, m.p. 204°–205° C. Found: C,59.11; H,6.15; N,10.55. $C_{26}H_{32}N_4O_6S$ requires C,59.08; H,6.10; N,10.60%.

EXAMPLE 5

2- [2 -Ethoxy-5-(N-2-ethoxycarbonylethyl-N-methyl-sulphamoyl) phenyl]-8-n-propylpyrido[3,2-d]pyrimidin-4(3H)-one Obtained using ethyl 3- (methylamino) propionate in 67% yield, m.p. 145°–146° C. Found: C,57.67; H,6.01; N,11.02. $C_{24}H_{30}N_4O_6S$ requires C,57.36; H,6.02; N,11.15%.

EXAMPLE 6

2-[2-Ethoxy-5-(methylsulphamoyl)phenyl]-8-n-propylprido [3,2-d]pyrimidin-4(3H)-one Obtained using methylamine (in ethanol solution) in 58% yield, m.p. 216°–219° C. Found: C,56.81; H,5.68; N,13.52. $C_{19}H_{22}N_4O_4S$ requires C,56.70; H,5.51; N,13.92%.

EXAMPLE 7

2-{2-Ethoxy-5-[4-(2-hydroxyethyl)-1-piperazinyl-sulphony ]phenyl}-8-n-propylprido[3.2-d ]pyrimidin-4(3H)-one Obtained using 1-(2-hydroxyethyl) piperazine in 34% yield, m.p. 187°–188° C. Found: C, 57.84; H, 6.19; N,13.64. $C_{24}H_{31}N_5O_5S$ requires C,57.46; H,6.23; N,13.96%.

EXAMPLE 8

2-{2-Ethoxy-5-[2-(1-imidazolidin-2-onyl)ethyl-sulphamoyl]phenyl}-8-n-propylprido[3,2-d]pryimidin-4 (3H)-one Obtained using 1-(2-aminoethyl)imidazolidin-2-one in 44% yield, m.p. 221°–222° C. Found: C,55.69; H,5.63; N,16.55. $C_{23}H_{28}N_6O_5S$ requires C,55.18; H,5.64; N,16.79%.

EXAMPLE 9

2-[5-(4-Carboxypiperidinosulphonyl)-2-ethoxyphenyl]-8-n-propylprido [3,2-d]pyrimidin-4(3H)-one A mixture of 2-[2-ethoxy-5-(4-ethoxycarbonyl-piperidinosulphonyl)phenyl]-8-n-propylpyrido[3,2-d]pyrimidin-4(3H)-one (Example 4; 0.55 g, 0.001 mol), potassium hydroxide (0.146 g, 0.0026 mol) and ethanol (35 ml) was stirred under reflux for 5 hours, then allowed to cool. The solvent was evaporated under vacuum, and the residue chromatographed twice on ion-exchange resin (Bio-rad AG50W-X8 H⁺, 27.5 g) using a pyridine in water elution gradient (2–50% pyridine). Crystallisation of the product from aqueous ethanol gave the title compound as a colourless solid (0.09 g, 8%), m.p. 262°–264° C. Found: C,57.51; H,5.68; N,11.10. $C_{24}H_{28}N_4O_6S$ requires C,57.58; H,5.64; N,11.19%.

EXAMPLE 10

2-(2-Ethoxy-5-nitrophenyl)-8-n-propylpyrido[3,2-d]-primidin-4(3H)-one

A solution of 2-(2-ethoxyphenyl)-8-n-propylpyrido-[3,2-d]pyrimidin-4(3H)-one (Preparation 8; 0.80 g, 0.0026 mol) in a mixture of concentrated sulphuric acid (5.4 ml) and concentrated nitric acid (0.20 ml) was stirred at ambient temperature for 4.5 hours. The mixture was then poured cautiously into stirred ice/water (50 g) and the resulting mixture extracted with a methanol:dichloromethane mixture (1:9, 3×50 ml). The organic extracts were combined, dried (MgSO₄) and evaporated under vacuum, and the residue crystallised from ethyl acetate:methanol to give the title compound as an off-white solid (0.71 g, 77%), m.p.257°–259° C. Found: C,61.28; H,5.11; N,15.60. $C_{18}H_{18}N_4O_4$ requires C,61.01; H,5.12; N,15.81%.

EXAMPLE 11

2-(5-Amino-2-ethoxyphenyl)-8-n-propylprido[3,2-d]-pyrimidin-4(3H) -one

Stannous chloride dihydrate (2.48 g, 0.011 mol) was added to a stirred solution of 2-(2-ethoxy-5-nitro-phenyl)-8-n-propylprido [3,2-d]pyrimidin-4(3H)-one (Example 10; 0.78 g, 0.0022 mol) in ethanol (10 ml) and the mixture was heated under reflux for 2 hours, allowed to cool, basified to pH 11 by the addition of 10% aqueous sodium hydroxide solution, and then extracted with methanol:dichloromethane (1:9, 3×50 ml). The organic extracts were combined, dried (MgSO₄) and evaporated under vacuum, then the residue was chromatographed on silica gel (12 g) using a methanol in dichloromethane elution gradient (0–2% methanol). Trituration of the product with hexane:ethyl acetate gave the title compound as a colourless solid (0.51 g, 71%), m.p. 156°–158° C. Found: C,66.61; H,6.20; N,17.14. $C_{18}H_{20}N_4O_2$ requires C,66.65; H,6.22; N,17.27%.

EXAMPLES 12 & 12A

2-{2-Ethoxy-5-[(bis-3-pyridylsulphonyl) amino]phenyl}-8-n-propylprido [3,2-d]pyrimidin-4(3H) -one and 2-[2-Ethoxy-5-(3-pyridylsulphonylamino) phenyl]-8-n-propylpyrido [3,2-d]pyrimidin-4(3H) -one 3-Pyridylsulphonyl chloride (0,201 g, 0.00113 mol) was added to a stirred mixture of 2-(5-amino-2-ethoxy-phenyl)-8-n-propylprido [3,2-d]pyrimidin-4(3H) -one (Example 11; 0.25 g, 0.00077 mol) and pyridine (5 ml), and the resulting mixture stirred at ambient temperature for 12 days and then added to water (50 ml). The resulting solution was acidified to pH 1 with 2N hydrochloric acid, and then extracted with methanol:dichloromethane (1:9, 3×50 ml). The combined extracts were dried (MgSO₄) and evaporated under vacuum and the residue chromatographed on silica gel (12 g) using a methanol in dichloromethane elution gradient (0–2% methanol). Crystallisation of the product from ethyl acetate-:methanol gave the first title compound as an off-white solid (0.123 g, 34%), m.p. 242°–243° C. Found: C,55.50; H,4.60; N,13.60. $C_{28}H_{26}N_6O_6S_2$ requires C,55.43; H,4.32; N,13.85%.

The aqueous phase was extracted further with methanol-dichloromethane (1:9, 3×50 ml), and the combined extracts dried (MgSO₄) and evaporated under vacuum. Chromatography of the residue on silica gel (12 g), using a methanol in dichloromethane elution gradient (2–5% methanol), followed by crystallisation of the product from ethyl acetate-:methanol, gave the second title compound as a white solid (0.104 g, 29%), m.p. 229°–231° C. Found: C,59.65; H,5.14; N,14.75. $C_{23}H_{23}N_5O_4S$ requires C,59.34; H,4.98; N,15.04.

EXAMPLE 13

2-[2-Ethoxy-5-(2-propylsulphonylamino) phenyl]-8n-propyl-pyrido [3,2-d]pyrimidin-4(3H)-one The title compound was prepared using 2-propyl-sulphonyl chloride following the procedure of Example 12 and was obtained as a white solid (55%), m.p. 207°–210° C. Found: C,58.32; H,6.06; N,12.81. $C_{21}H_{26}N_4O_4S$ requires C,58.59; H,6.09; N,13.01%.

EXAMPLE 14

2-[2-Ethoxy-5-(4-methyl-1-piperazinylsulphbonyl) phenyl]-pyrido[3,2-d]pyrimidin-4(3H) -one 2-(2-Ethoxyphenyl)pyrido[3,2-d]pyrimidin-4(3H)-one (Preparation 10; 1.2 g, 0.0045 mol) was added portion-wise to stirred chlorosulphonic acid (6 ml) under a nitrogen atmosphere at 0° C. The mixture was stirred at ambient temperature for 18 hours and then added cautiously to ice/water (100 g). The resulting solution was brought to pH 5 by the addition of saturated aqueous sodium carbonate solution and then extracted with dichloromethane methanol (9:1, 3×150 ml). The organic fractions were combined, dried (MgSO₄) and evaporated under vacuum to give the sulphonyl chloride, which was used without further purification.

The crude sulphonyl chloride (0.55 g, 0.0015 mol) was added to a stirred solution of 1-methylpiperazine (0.45 g, 0.0045 mol) in ethanol (10 ml), and the resulting solution stirred at ambient temperature for 18 hours. The solvent was evaporated under vacuum and the residue chromatographed on silica gel (10 g), eluting with a mixture of dichloromethane:methanol: 0.880 aqueous ammonia solution (95:5:1). Crystallisation of the product from ethyl acetate: methanol gave the title compound as a white solid (0,325 g, 51%), m.p. 212°–215° C. Found: C,56.03; H,5.44; N,16.55. $C_{20}H_{23}N_5O_4S$ requires C,55.93; H,5.40; N,16.31%.

The following four compounds were obtained from the same sulphonyl chloride and the appropriate amine by procedures similar to that described in Example 14.

EXAMPLE 15

2-{2-Ethoxy-5[(bis-2-hydroxyethl)sulphamoyl]phenyl}-pyrido [3,2-d]pyrimidin-4(3H)-one Obtained using diethanolamine in 37% yield, m.p. 223°–225° C. Found: C,52.26; H,4.97; N,13.00. $C_{19}H_{22}N_4O_6S$ requires C,52.52; H,5.10; N,12.96%.

EXAMPLE 16

2-{2-Ethoxy-5-[(2-pyridylmethyl)sulphamoyl]phenyl}-pyrido [3,2-d]pyrimdin-4(3H)-one Obtained using 2-aminomethylpyridine in 50% yield, m.p. 230°–231° C. Found: C,57.64; H,4.42; N,16.22. $C_{21}H_{19}N_5O_4S$ requires C, 57.66; H, 4.38; .N, 16.01%.

EXAMPLE 17

2-{2-Ethoxy-5-[(5-isoxazolin-3-onylmethyl)sulphamoyl]-phenyl}pyrido [3,2-d]pyrimidin-4(3H)-one Obtained using muscimol hydrate in 32% yield, m.p. indeterminate (amorphous solid). Rf 0.40 (dichloromethane: methanol: glacial acetic acid, 90:10:1). Found: C,51.01; H,3.86; N,15.49. $C_{19}H_{17}N_5O_6S$ requires C,51.46; H,3.86; N,15.79%.

EXAMPLE 18

2-[5-(5-Amino-3hydroxy-1-pyrazolylsulphonyl)-2-ethoxy-phenyl]pyrido[3,2-d]pyrimidin-4(3H)-one Obtained using 3-amino-5-hydroxypyrazole in 34% yield, m.p. 246°–249° C. Found: C,50.69; H,3.70; N,19.28. $C_{18}H_{16}N_6O_5S$ requires C,50.46; H,3.76; N,19.62%.

EXAMPLE 19

2-(2-Ethoxy-5-nitrophenyl)pyrido[3,2-d]pyrimidin-4(3H)-one

A stirred solution of 2-(2-ethoxyphenyl)-pyrido[3,2-d] pyrimidin-4(3H)-one (Preparation 10; 1.4 g, 0.0052 mol)in concentrated sulphuric acid (11 ml) at 0° C., was treated dropwise with concentrated nitric acid (0.4 ml). The reaction mixture was allowed to warm to ambient temperature, stirred for a further 18 hours, then added dropwise to ice/water (70 g). The resulting precipitate was collected by filtration, dried under vacuum and then crystallised from acetonitrile to give the title compound as a pale yellow solid (0.22 g, 86%), m.p. 251°–254° C. Found: C,57.69; H,3.87; N,17.94. $C_{15}H_{12}N_4O_4$ requires C,57.41; H,3.82; N,18.37%.

EXAMPLE 20

2- (5-Amino-2-ethoxyphenyl)pyrido [3,2-d]pyrimidin-4(3H)-one

A stirred mixture of 2-(2-ethoxy-5-nitrophenyl)-pyrido[3, 2-d]pyrimidin-4(3H)-one (Example 19; 1.1 g, 0.00353 mol), stannous chloride dehydrate (4.0 g, 0.0177 mol) and ethanol (15 ml) was heated under reflux for 4 hours. The resulting mixture was allowed to cool, diluted with water (15 ml), adjusted to pH 8 with 2N aqueous sodium hydroxide solution, vigorously shaken with dichloromethane (30 ml), and then this mixture filtered. The aqueous phase was separated and extracted further with dichloromethane (2×30 ml), and the organic extracts were then combined, dried (MgSO$_4$) and evaporated under vacuum. Crystallisation of the product from acetonitrile gave the title compound as a hydrated yellow solid (0.72 g, 72%), m.p. 208°–210° C. Found: C,62.88; H,4.88; N,19.67. $C_{15}H_{14}N_4O_2;0.25H_2O$ requires C,62.81; H,5.10; N,19.54%.

EXAMPLE 21

2-[2-Ethoxy-5-(2-propylsulphonylamino)phenyl]pyrido-[3,2-d]pyrimidin-4(3H)-one

The title compound was prepared using 2-propyl-sulphonyl chloride and 2-(5-amino-2-ethoxyphenyl)-pyrido[3,2-d] pyrimidin-4(3H)-one (Example 20), following the procedure of Example 12, and was obtained as a hydrated solid (59%), m.p. 211°–213° C. Found: C,54.98; H,5.07; N;14.21. $C_{18}H_{20}N_4O_4S;0.25$ $H_2O$ requires C,55.02; H,5.26; N,14.26%.

EXAMPLE 22

2-(5-Isobutyrylamino-2-ethoxphenyl)pyrido[3,2-d]pyrimidin-4(3H)-one

The title compound was prepared using isobutyryl chloride and 2-(5-amino-2-ethoxyphenyl) pyrido[3,2-d]pyrimidin-4(3H)-one (Example 20), following the procedure of Example 12, and was obtained as a white solid (80%), m.p. 256°–259° C. Found:C,64.48; H,5.86; N,15.75. $C_{19}H_{20}N_4O_3S$ requires C,64.76; H,5.72; N,15.90%.

EXAMPLE 23

8-cyano-2-[2-ethoxy-5-(1-piperazinylsulphonyl)phenyl]-pyrido [3,2-d]pyrimidin-4(3H)-one The title compound was prepared from 8-cyano-2-(2-ethoxyphenyl ) pyrido[3,2-d]pyrimidin-4(3H)-one (Preparation 14) and piperazine, following the procedure of Example 1, and was obtained as an off-white solid (22%), m.p. 172°–175° C. Found: C,54.09; H,4.70; N,18.71. $C_{20}H_{20}N_6O_4S$ requires C,54.53; H,4.58; N, 19 . 08%.

EXAMPLE 24

8-Cyano-2-[2-ethoxy-5-(4-methyl-1-piperazinyl-sulphonyl) phenyl]pyrido[3,2d]pyrimidin-4(3H)-one The title compound was prepared from 8-cyano-2-(2-ethoxyphenyl) pyrido[3,2-d]pyrimidin-4(3H)-one (Preparation 14 ) and 1-methylpiperazine, following the procedure of Example 1, and was obtained as an off-white solid (8%), m.p. 239°–240° C. Found: C,55.61; H,4.93; N,18.60. $C_{21}H_{22}N_6O_4S$ requires C,55.49; H,4.88; N,18.49%.

EXAMPLE 25

8-Carbamoyl -2-[2-ethoxy-5-(4-methyl-1-piperazinylsulphonyl) phenyl]pyrido[3,2-d]pyrimidin-4(3H)-one The title compound was prepared from 8-carbamoyl-2-(2-ethyoxyphenyl) pyrido[3,2-d]pyrimidin-4(3H)-one (Preparation 16) and 1-methylpiperazine, following the procedure of Example 1, and was obtained as a solvated white powder (13%), m.p. 237°–238° C. Found: C,49.86; H,4.93;

N,16.14. $C_{21}H_{24}N_6O_5S;0.60$ $CH_2Cl_2$ requires C,49.69; H,4.75; N,16.12%.

PREPARATION 1

Diethyl 4-n-propylpyridine-2,3,-dicarboxylate

A solution of diethyl 3-chloro-2-oxosuccinate (137.4 g, 0.69 mol), hexen-2-al (72.5 g, 0.74 mol) and ammonium sulphamate (190.2 g, 1.66 mol) in ethanol (450 ml) was stirred under reflux for 36 hours and then filtered. The filtrate was evaporated under vacuum, the resulting residue dissolved im water (500 ml) and this solution extracted with ethyl acetate (6×500 ml). The combined organic extracts were dried ($MgSO_4$) and evaporated under vacuum, then the resulting residue was chromatographed on silica gel (50 g), using an ethyl acetate in hexane elution gradient (0–20% ethyl acetate), to give the title compound as an orange oil (34.1 g, 21%). Rf 0.20 (ethyl acetate:hexane, 20:80).

PREPARATION 2

4-n-Propylpyridine-2,3-dicarboxamide

A mixture of liquid ammonia (40 ml) and diethyl 4-n-propylpyridine-2,3-dicarboxylate (Preparation 1; 2.0 g, 0.0075 mol) was heated in an autoclave at 100° C. for 18 hours and then allowed to cool. The ammonia was allowed to evaporate, then the residue was azeotroped with methanol and crystallised from ethyl acetate: methanol to give the title compound as a colourless solid (0.1 g, 6.4%), m.p. 178°–179° C. Found: C,57.73; H,6.45; N,19.85. $C_{10}H_{13}N_3O_2$ requires C,57.96; H,6.32; N,20.28%.

PREPARATION 3

7-n-Propyl-4-azaphthalimide

A stirred solution of 4-n-propylpyridine-2,3-dicarboxamide (Preparation 2; 0.1 g, 0.00048 mol) in N,N-dimethylacetamide (10 ml) was heated at 160° C. for 5 hours and then the solvent was evaporated under vacuum. The residue was purified by chromatography on silica gel (5 g), eluting with a solution of 3% methanol in dichloromethane, followed by crystallisation from ethyl acetate to give the title compound as a light yellow solid (0.014 g, 15%), m.p. 163°–165° C. Found: C,63.41; H,5.35; N,15.04. $C_{10}H_{10}N_2O_2$ requires C,63.15; H,5.30; N,14.73%.

PREPARATION 4

3-Amino-4-n-propylpyridine-2-carboxylic acid

A stirred solution of 7-n-propyl-4-azaphthalimide (Preparation 3; 1.9 g, 0.010 mol) in aqueous sodium hydroxide solution (2.8 g, 0.07 mol of NaOH in 30 ml of water) was treateed with aqueous sodium hypochlorite solution (5 ml, 0.010 mol). The resulting mixture was heated at 80° C. for 0.5 hour, cooled and acidified with dilute sulphuric acid (50%, 2 ml). The suspension produced was filtered and the solid thus obtained was crystallised from water to give the title compound as an off-white solid (0.38 g, 21%), m.p. 185°–188° C. Found: C,59.34; H,6.63; N,15.35. $C_9H_{12}N_2O_2$ requires C,59.98; H,6.71; N,15.55%.

PREPARATION 5

Ethyl 3-amino-4-n-propylpyridine-2-carboxylate

3-Amino-4-n-propylpyridine-2-carboxylic acid (Preparation 4; 0.36 g, 0.002 mol) was added to a stirred mixture of cesium carbonate (0,325 g, 0.001 mol) in water (20 ml), then this mixture was evaporated under vacuum and the residue azeotroped with dimethylformamide (2×20 ml). The resulting cesium salt was suspended in dimethylformamide (3 ml) and the stirred suspension then treated dropwise with ethyl iodide (0.17 ml, 0.0021 mol). After a further 0.25 hour, the solvent was evaporated under vacuum and the residue partitioned between water (20 ml) and ethyl acetate (20 ml). The organic phase was washed with water (10 ml), dried ($MgSO_4$) and evaporated under vacuum, then the residue crystallised from acetone:hexane to give the title compound as an off-white solid (0.35 g, 84%), m.p. 93°–96° C. Found: C,63.39; H,7.73; N,13.39. $C_{11}H_{16}N_2O_2$ requires C,63.44; H,7.74; N,13.45%.

PREPARATION 6

3-Amino-4-n-propylpyridine-2-carboxamide

A mixture of ethyl 3-amino-4-n-propylpyridine-2-carbolate (Preparation 5; 7.4 g, 0.035 mol) and liquid ammonia (60 ml) was heated in an autoclave at 00° C for 18 hours. The mixture was allowed to cool and the ammonia to evaporate, then the residue was crystallised from methanol to give the title compound as a colourless solid (4.84 g, 76%), m.p. 139°–141° C. Found: C,60.32; H,7.27; N,23.56. $C_9H_{13}N_3O$ requires C,60.31; H,7.31; N,23.45%.

PREPARATION 7

3-(2-Ethoxybenzoylamino)-4-n-propylpyridine-2-carboxamide

2-Ethoxybenzoyl chloride (2.96 g, 0.016 mol) was added dropwise to a stirred solution of 3-amino-4-n-propylpridine-2-carboxamide (Preparation 6; 1.43 g, 0.008 mol) in pyridine (40 ml) at 0° C. The mixture was stirred at ambient temperature for 4 hours and then the solvent evaporated under vacuum. The residue was dissolved in dichloromethane (100 ml), the solution washed with saturated aqueous sodium carbonate solution (100 ml) and the aqueous phase then washed with dichloromethane (2×25 ml). The combined organic extracts were dried ($MgSO_4$) and evaporated under vacuum, then the residue purified by chromatography on silica gel (15 g), using a methanol in dichloromethane elution gradient (0–3% methanol), followed by crystallisation from ethyl acetate to give the product as a light brown solid (1.36 g, 60%), 129°–131° C. Found: C,66.29; H,6.53; N,12.78. $C_{18}H_{21}N_3O_3$ requires C,66.04; H,6.47; N,12.84%.

PREPARATION 8

2-(2-Ethoxyphenyl)-8-n-propylpyrido[3,2-d]pyrimidin-4(3H)-one

A mixture of 3-(2-ethoxybenzoylamino)-4-n-propylpridine-2-carboxamide (Preparation 7; 1.52 g, 0.0046 mol) and anhydrous zinc chloride (1.88 g, 0.014 mol) was heated at 210° C. for 0.25 hour. The cool mixture was dissolved in methanol (20 ml) and this solution poured into an aqueous solution of disodium ethylenediamine tetraacetic acid (10.3 g in 200 ml water). The resulting mixture was basified with saturated aqueous sodium carbonate solution (20 ml), then extracted with dichloromethane (4×60 ml). The combined organic extracts were dried ($MgSO_4$) and evaporated under vacuum, then the residue crystallised from ethyl acetate to give the title compound as a white solid (0.92 g, 65%), m.p. 134°–137° C. Found: C,69.69; H,6.27; N,13.54. $C_{18}H_{19}N_3O_2$ requires C,69.88; H,6.19; N,13.58%.

PREPARATION 9

3-(2-Ethoxybenzoylamino)pyridine-2-carboxamide

The title compound was prepared from 2-ethoxybenzoyl chloride and 3-aminopyridine-2-carboxamide (J. Chem. Soc., 1956, 1045) following the procedure of Preparation 7 and was obtained as an off-white solid (100 %), m.p. 172°–177° C. Found: C,62.91; H,5.30; N,14.51. $C_{15}H_{15}N_3O_3$ requires C,63.15; H,5.30; N,14.73%.

PREPARATION 10

2-(2-Ethoxyphenyl)pyrido[3,2-d]pyrimidin-4(3H)-one

The title compound was prepared from 3-(2-ethoxybenzoylamino) pyridine-2-carboxamide (Preparation 9) following the procedure of Preparation 8 and was obtained as an off-white solid (56%), m.p. 184°–187° C. Found: C, 67.24; H, 4.87; N, 15.76. $C_{15}H_{13}N_3O_2$ requires C,67.40; H,4.90; N,15.72%.

PREPARATION 11

Ethyl 3-amino-4-cyanopyridine-2-carboxylate

A stirred solution of ethyl 2-cyano-2-(formylamino)acetate J. Org. Chem., 1979, 44, 3835; 0.47 g, 0.003 mol), acrylonitrile (1.2 ml, 0.018 mol) and trifluoroacetic acid (0.02 ml, 0.0003 mol) in 1,2-dichloroethane (4 ml) was heated under reflux for 3 days. The solvent was removed by evaporation under vacuum, the residue dissolved in dichloromethane (30 ml) and the resulting solution washed with saturated aqueous sodium bicarbonate solution (30 ml). The aqueous phase was washed with dichloromethane (30 ml) and the organic solutions then combined, dried ($MgSO_4$) and evaporated under vacuum. Chromatography of the residue on silica gel (12 g), eluting with dichloromethane:methanol (100:1), followed by crystallisation from acetone: hexane, gave the title compound as a colourless solid (0.12 g, 21%), m.p. 114°–116° C. Found: C,56.89; H,4.75; N,22.08. $C_9H_9N_3O_2$ requires C,56.54; H,4.75; N,21.98%.

PREPARATION 12

3-Amino-4-cyanopyridine-2-carboxamide

A mixture of liquid ammonia (30 ml) and ethyl 3-amino-4-cyanopyridine-2-carboxylate (Preparation 11; 2.8 g, 0.0147 mol) was heated at 100° C. in an autoclave for 18 hours. The ammonia was allowed to evaporate and the resulting product crystallised from ethyl acetate to give the title compound as an off-white solid (2.2 g, 94%), m.p. >310° C. Found: C,51.84; H,3.69; N,34.30. $C_7H_6N_4O$ requires C,51.85; H,3.73; N,34.56%.

PREPARATION 13

4-Cyano-3-(2-ethoxybenzylamino)pyridine-2-carboxamide

The title compound was prepared from 2-ethoxybenzoyl chloride and 3-amino-4-cyanopyridine-2-carboxamide (Preparation 12), following the procedure of Preparation 7, and was obtained as a colourless solid. (6.2%), m.p. 150°–152° C. Found: C,61.99; H,4.62; N,17.84. $C_{16}H_{14}N_4O_3$ requires C,61.93; H,4.55; N,18.06%.

PREPARATION 14

8-Cyano-2-(2-ethoxyphenyl)pyrido[3,2-d]pyrimidin-4(3H)-one

The title compound was prepared from 4-cyano-3-(2-ethoxybenzoylamino) pyridine-2-carboxamide (Preparation 13), following the procedure of Preparation 8, and was obtained as a white solid (54%), m.p. 255°–256° C. Found: C,66.03; H,4.10; N,19.08. $C_{16}H_{12}N_4O_2$ requires C,65.75; H,4.14; N,19.17%.

PREPARATION 15

8-Carbamoyl-2-(2-ethoxyphenyl)pyrido[3,2-d]pyrimidin-4(3H)-one

30% Aqueous hydrogen peroxide solution (0.5 ml) was added to a stirred aqueous sodium hydroxide solution (1M, 40 ml), followed by 8-cyano-2-(2-ethoxyphenyl)pyrido[3,2-d]pyrimidin-4(3H)-one (Preparation 14; 0.2 g, 0.00068 mol) and ethanol (2 ml). The mixture was heated under reflux for 2 hours, allowed to cool, acidified with 1N hydrochloric acid, and then extracted with a mixture of dichloromethane and methanol (10:1, 5×50 ml). The combined organic fractions were evaporated under vacuum and the resulting residue triturated with ethanol to give the title compound as a colourless solid (0.152 g, 72%), m.p. 295°–297° C. Found: C,61.65; H,4.56; N,17.61. $C_{16}H_{14}N_4O_3$ requires C,61.93; H,4.55; N,18.06%.

Biological activity

The following Table illustrates the in vitro activities for a range of the compounds of the invention.

TABLE

IN VITRO PDE INHIBITORY DATA: SELECTIVITY BETWEEN CALCIUM/CALMODULIN (Ca/CAM)-INDEPENDENT cGMP PDE AND cGMP-INHIBITED cAMP PDE

| EXAMPLE | $IC_{50}$ (nM) cGMP | cAMP | SELECTIVITY RATIO |
| --- | --- | --- | --- |
| 1 | 21 | 19,000 | 904 |
| 2 | 26 | 13,000 | 500 |
| 4 | 5.6 | 7,600 | 1,357 |
| 5 | 14 | 8,300 | 592 |
| 7 | 9.8 | 11,000 | 1,122 |
| 9 | 1.2 | 220 | 183 |
| 12A | 19 | 4,600 | 242 |
| 24 | 25 | >100,000 | >4,000 |

Safety Profile

Examples 7 and 9 have been tested at doses of up to 0.1 mg/kg and 1 mg/kg i.v. respectively, Examples 1 and 8 at doses of up to 3 mg/kg i.d. and Example 3 at doses of up to 10 mg/kg i.d., in rabbit, with no untoward effects being observed.

We claim:

1. A compound of formula (I):

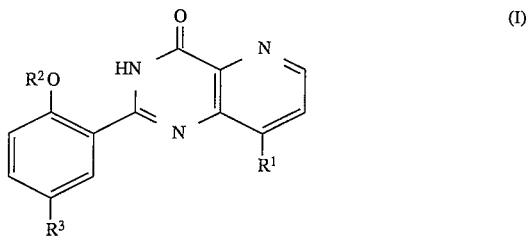

or a pharmaceutically acceptable salt thereof, wherein $R^1$ is H, $C_1$–$C_4$ alkyl, CN or $CONR^4R^5$;

$R^2$ is $C_2$–$C_4$ alkyl;

$R^3$ is $SO_2NR^6R^7$, $NO_2$, $N_3$, $NHCOR^8$, $NHSO_2R^8$ or $N(SO_2R^8)_2$;

$R^4$ and $R^5$ are each independently selected from H and $C_1$–$C_4$ alkyl;

$R^6$ and $R^7$ are each independently selected from H and $C_1$–$C_4$ alkyl optionally substituted with $CO_2R^9$, OH, pyridyl, 5-isoxazolin-3-onyl, morpholino or 1-imidazolidin-2-onyl; or together with the nitrogen atom to which they are attached form a pyrrolidino, piperidino, morpholino, 1-pyrazolyl or 4-($NR^{10}$)-1-piperazinyl group wherein any of said groups may optionally be substituted with one or two substituents selected from $C_1$–$C_4$ alkyl, $CO_2R^9$, $NH_2$ and OH;

$R^8$ is $C_1$–$C_4$ alkyl or pyridyl;

$R^9$ is H or $C_1$–$C_4$ alkyl;

and $R^{10}$ is H, $C_1$–$C_4$ alkyl or (hydroxy)$C_2$–$C_3$ alkyl.

2. A compound according to claim 1 wherein $R^1$ is H, n-propyl, CN or $CONH_2$; $R^2$ is ethyl; $R^3$ is $SO_2NR^6R^7$, $NO_2$, $NH_2$, $NHCOCH(CH_3)_2$, $NHSO_2CH(CH_3)_2$, $NHSO_2$(3-pyridyl) or $N[SO_2$(3-pyridyl)$]_2$; $R^6$ is H, methyl or 2-hydroxyethyl; $R^7$ is methyl optionally substituted with 2-pyridyl or 5-isoxazolin-3-onyl, or ethyl 2-substituted with OH, $CO_2CH_2CH_3$, morpholino or 1-imidazolidin-2-onyl, or $R^6$ and $R^7$ together with the nitrogen atom to which they are attached form a (4-$CO_2R^9$) piperidino, 5-amino-3-hydroxy-1-pyrazolyl or 4-($NR^{10}$)-1-piperazinyl group; $R^9$ is H or ethyl; and $R^{10}$ is H, methyl or 2-hydroxyethyl.

3. A compound according to claim 2 wherein $R^1$ is n-propyl or CN; $R^2$ is ethyl; $R^3$ is $SO_2NR^6R^7$, $NHSO_2CH(CH_3)_2$, $NHSO_2$(3-pyridyl) or $N[SO_2$(3-pyridyl)$]_2$; $R^6$ is H or methyl; $R^7$ is methyl, or ethyl 2-substituted with $CO_2CH_2CH_3$, morpholino or 1-imidazolidin-2-onyl, or $R^6$ and $R^7$ together with the nitrogen atom to which they are attached form a (4-$CO_2R^9$)piperidino or 4-($NR^{10}$)-1-piperazinyl group; $R^9$ is H or ethyl; and $R^{10}$ is H, methyl or 2-hydroxyethyl.

4. A compound according to claim 3 wherein the said compound of formula (I) is selected from 2-[2-ethoxy-5-(4-ethoxycarbonylpiperidino-sulphonyl) phenyl]-8-n-propylpyrido[3,2-d]pyrimidin-4(3H)-one;

2-[5-(4-carboxypiperidinosulphonyl)-2-ethoxyphenyl]-8-n-propylpyrido [3,2-d]pyrimidin-4(3H)-one;

2-{2-ethoxy-5-[4-(2-hydroxyethyl)-1-piperazinyl-sulphonyl]phenyl}-8-n-propylpyrido[3,2-d]pyrimidin-4(3H)-one p1 and 2-{2-ethoxy-5-[(bis-3-pyridylsulphonyl)amino]-phenyl}-8-n-propylpyrido[3,2-d] pyrimidin-4(3H)-one.

5. A pharmaceutical composition comprising a compound of formula (I), or a pharmaceutically acceptable salt thereof, according to claim 1, together with a pharmaceutically acceptable diluent or carrier.

6. A method of treating or preventing stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterized by disorders of gut motility, in a mammal, which comprises administering to said mammal a therapeutically effective amount of a compound of formula (I), or a pharmaceutically acceptable salt thereof, or a pharmaceutical composition containing either entity, according to claim 1.

7. A method of treating or preventing stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterized by disorders of gut motility, in a mammal, which comprises administering to said mammal a therapeutically effective amount of a compound of formula (I), or a pharmaceutically acceptable salt thereof, or a pharmaceutical composition containing either entity, according to claim 5.

8. A compound of formula (III):

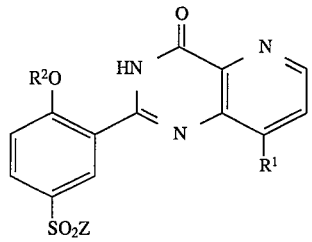

(III)

wherein Z is halo; $R^1$ is H, $C_1$–$C_4$ alkyl, CN or $CONR^4R^5$; $R^2$ is $C_2$–$C_4$ alkyl; and $R^4$ and $R^5$ are each independently selected from H and $C_1$–$C_4$ alkyl.

9. A compoiund of formula (II):

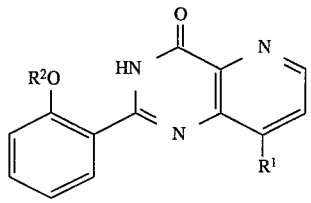

(II)

wherein $R^1$ is CN or $CONR^4R^5$;

$R^2$ is $C_2$–$C_4$ alkyl; and $R^4$ and $R^5$ are each independently selected from H and $C_1$–$C_4$ alkyl.

* * * * *